United States Patent [19]
Akemi et al.

[11] Patent Number: 5,298,258
[45] Date of Patent: Mar. 29, 1994

[54] ACRYLIC OILY GEL BIOADHESIVE MATERIAL AND ACRYLIC OILY GEL PREPARATION

[75] Inventors: Hitoshi Akemi; Takashi Kinoshita; Saburo Otsuka; Yoshifumi Hosaka; Yoshihisa Nakano, all of Osaka, Japan

[73] Assignee: Nitto Denko Corporation, Osaka, Japan

[21] Appl. No.: 899,278

[22] Filed: Jun. 16, 1992

Related U.S. Application Data

[63] Continuation-in-part of Ser. No. 635,007, Dec. 28, 1990, abandoned.

[30] Foreign Application Priority Data

Dec. 28, 1989 [JP] Japan .................. 1-344639
Sep. 6, 1990 [JP] Japan .................. 2-237382

[51] Int. Cl.$^5$ ............................. A61K 9/14
[52] U.S. Cl. ............................ 424/484; 424/486; 424/487
[58] Field of Search ............... 526/310; 562/598; 525/330.2; 424/484, 78.26, 78.34, 78.18, 484, 486, 487

[56] References Cited

U.S. PATENT DOCUMENTS

| | | | |
|---|---|---|---|
| 2,647,884 | 8/1953 | Wystrach | 526/310 |
| 3,380,947 | 4/1968 | Galgoczi et al. | 562/598 |
| 3,404,134 | 10/1968 | Rees | 525/329.9 |
| 4,608,249 | 8/1986 | Otsuka et al. | 424/484 |
| 4,615,697 | 10/1986 | Robinson | 604/890 |
| 4,676,254 | 6/1987 | Kamishita | 424/78.05 |
| 4,771,105 | 9/1988 | Shirai et al. | 525/330.2 |
| 5,002,986 | 3/1991 | Fujiura et al. | 525/330.2 |
| 5,003,012 | 3/1991 | Chamberlain et al. | 525/330.2 |

FOREIGN PATENT DOCUMENTS

| | | |
|---|---|---|
| 0223524 | 5/1987 | European Pat. Off. |
| 0303445 | 2/1989 | European Pat. Off. |
| 0309404 | 3/1989 | European Pat. Off. |
| 0319988 | 6/1989 | European Pat. Off. |
| 1023895 | 3/1966 | United Kingdom |
| 2086224 | 5/1982 | United Kingdom |

*Primary Examiner*—Thurman K. Page
*Assistant Examiner*—Peter F. Kulkosky
*Attorney, Agent, or Firm*—Sughrue, Mion, Zinn, Macpeak & Seas

[57] ABSTRACT

An acrylic oily gel bioadhesive material comprising a substrate having on one surface thereof a crosslinked gel layer formed by crosslinking a composition comprising an acrylate polymer comprising as a main component an alkyl (meth)acrylate having four or more carbon atoms in the alkyl moiety and a liquid ingredient compatible with said acrylate polymer.

9 Claims, No Drawings

ACRYLIC OILY GEL BIOADHESIVE MATERIAL AND ACRYLIC OILY GEL PREPARATION

CROSS-REFERENCE TO THE RELATED APPLICATION

This application is a continuation-in-part application of U.S. patent application Ser. No. 07/635,007 filed on Dec. 28, 1990, now abandoned, entitled "ACRYLIC GEL MATERIAL AND ACRYLIC GEL PREPARATION", now pending.

FIELD OF THE INVENTION

The present invention relates to an acrylic oily gel bioadhesive material which is applied to a surface of a skin so as to protect the skin surface and an acrylic oily gel preparation which is used to continuously administer a drug component to a living body via the skin surface.

BACKGROUND OF THE INVENTION

Recently, various percutaneous preparations for external use in the form of a preparation applied to the skin (for example, plaster, tape), whereby a drug is administered to the living body via the skin surface, have been developed.

Such a percutaneous preparation applied to the skin usually involves an adhesive layer having a relatively large adhesiveness to secure the fixation of the preparation on the skin surface. Alternatively, the entire preparation is covered with a highly adhesive sheet having a large adhesiveness which secures the fixation of the preparation on the skin.

Although a percutaneous preparation applied to the skin should be surely fixed on the skin so as to secure the migration of a drug component into the skin, an excessively large adhesiveness might bring about a pain or peeling of the horny substance caused by physical stimulation upon the separation of the preparation from the skin surface. Further, serious skin irritation is sometimes observed.

Thus, the adhesiveness to the skin is an important factor in the development of a percutaneous preparation in practice, and the problem of the skin irritation is also an important factor. Therefore, it has been practically required to develop a preparation which scarcely irritates the skin and can be securely fixed onto the skin.

SUMMARY OF THE INVENTION

Under these circumstances, the present inventors have conducted extensive studies to overcome the above problems. As a result, it has been found that a composition comprising an acrylate polymer and a liquid ingredient compatible with the acrylate polymer, in which the liquid ingredient is used in an amount larger than a common level, can achieve a softness upon the adhesion to the skin. However, it has been further found that such a composition as described above suffers from a serious decrease in the cohesive power and thus causes cohesion breakage, which makes the peeling of the composition from the skin impossible or brings about skin irritation. Thus, such a preparation cannot be used in practice. Furthermore, it has been found that a decrease in the cohesive power of the composition can be prevented and the stress applied to the skin surface upon the separation of a composition can be relieved and dispersed so as to achieve well-balanced skin adhesiveness and skin irritativeness by crosslinking a polymer layer containing an excessive amount of a liquid ingredient to thereby form a so-called oily gel, thus completing the present invention.

An object of the present invention is to provide an acrylic oily gel bioadhesive material applied to the skin surface.

Another object of the present invention is to provide an acrylic oily gel preparation capable of continuously administering a drug component to the living body.

The present invention provides an acrylic oily gel bioadhesive material comprising a substrate having on one surface thereof a crosslinked gel layer formed by crosslinking a composition comprising an acrylate polymer comprising as a main component an alkyl (meth)acrylate having 4 or more carbon atoms and a liquid ingredient compatible with the acrylate polymer.

The present invention also relates to an acrylic oily gel preparation wherein a drug component is contained in the above acrylic oily gel bioadhesive material.

DETAILED DESCRIPTION OF THE INVENTION

The substrate used in the acrylic oily gel bioadhesive material and the acrylic oily gel preparation of the present invention is not particularly limited, but materials which would never suffer from any decrease in the content of the liquid ingredient or the drug contained in the crosslinked gel layer caused by the migration toward another face of the substrate followed by leakage, are preferably used. Examples thereof include sole films of polyester, nylon, Saran resins, polyethylene, polypropylene, ethylene-vinyl acetate copolymer, polyvinyl chloride, ethylene-ethyl acrylate copolymer, polytetrafluoroethylene, Surlyn resins and metal foils, and laminate films comprising these materials. Of those, it is preferred to use a substrate in the form of a laminate film composed of a nonporous sheet comprising one or more materials as described above and a porous film and to form a crosslinked gel layer on the surface of the porous sheet, to thereby improve the adhesiveness between the substrate and the crosslinked gel layer by the anchoring effect which will be described hereinbelow.

The material of the porous film is not particularly restricted so long as the anchoring effect to the crosslinked gel layer can be improved. Examples thereof include paper, woven fabric, nonwoven fabric and mechanically perforated sheet. It is particularly preferred to use paper, woven fabric and nonwoven fabric. When the improvement of the anchoring effect and the flexibility of the whole preparation are taken into consideration, the thickness of the porous film is preferably from 10 to 500 $\mu$m, and in the case of a thin preparation such as plaster or tape, it is more preferably from 10 to 200 $\mu$m. When the laminate film composed of the above porous film and the nonporous sheet is used as the substrate, the thickness of the nonporous sheet is preferably from 0.5 to 50 $\mu$m, and more preferably from 1 to 25 $\mu$m.

When woven fabric or nonwoven fabric is used as the porous film, the weight per unit area of the woven or nonwoven fabric is preferably from 5 to 30 $g/m^2$, more preferably from 8 to 20 $g/m^2$, from the standpoint of the improvement on the anchoring effect.

In the present invention, the crosslinked gel layer formed on one surface of the substrate is a layer of a crosslinked structure obtained by crosslinking a composition comprising an acrylate polymer and a liquid ingredient compatible with the acrylate polymer together with, in the case of a preparation, a drug component, and having an appropriate adhesiveness to the skin and an appropriate cohesive power. The adhesiveness is generally from 40 o 250 g/12 mm width in terms of the adhesiveness to a bakelite plate (the determination method therefor will be described in detail hereinafter) and from 20 to 80 g in the probe-tack test.

The acrylate copolymer serves as a main component constituting the crosslinked gel layer together with the liquid ingredient which will be described in detail hereinafter. It sustains a high compatibility with the liquid ingredient and thus shows an excellent adhesiveness to the skin surface as well as an excellent shape retention. In the present invention, it is not preferred to use rubber such as natural or synthetic rubber or a silicone polymer since these materials have a poor compatibility with the liquid ingredient used in the present invention or show a considerably low solubility or release of the drug component. In addition, it is difficult to control the amount of functional groups participating in the crosslinking of such a polymer, as compared with the acrylate polymer used in the present invention, and thus highly reproducible crosslinking can hardly be achieved. These facts indicate that the abovedescribed polymers are unsuitable in the present invention.

The acrylate polymer used in the present invention is a polymer of an alkyl (meth)acrylate having 4 or more carbon atoms in the alkyl moiety. It is particularly preferred, from the standpoint of the convenience in the crosslinking, to use a copolymer obtained using the alkyl (meth)acrylate as the main component.

The terms "(meth)acrylate", etc. used herein mean "acrylate and/or methacrylate", etc.

Examples of the alkyl (meth)acrylate include (meth)acrylates having straight-chain or branched alkyl groups, for example, butyl, pentyl, hexyl, heptyl, octyl, nonnyl, decyl, undecyl, dodecyl and tridecyl. Either one or more of these (meth)acrylates can be used. Of these, 2-ethylhexyl acrylate, isooctyl acrylate and isononyl acrylate are preferably used.

Examples of a monomer to be copolymerized with the alkyl (meth)acrylate include monomers containing a carboxyl group, such as (meth)acrylic acid, itaconic acid, maleic acid and maleic anhydride; monomers containing a sulfoxyl group, such as styrenesulfonic acid, allylsulfonic acid, sulfopropyl (meth)acrylate, (meth)acryloyloxynaphthalenesulfonic acid and acrylamidemethyl propanesulfonic acid; monomers containing a hydroxyl group, such as hydroxyethyl (meth)acrylate and hydroxypropyl (meth)acrylate; monomers containing an amide group, such as (meth)acrylamide, diacetone acrylamide, dimethyl(meth)acrylamide, N-butylacrylamide, N-methylol(meth)acrylamide and N-methylolpropane(meth)acrylamide; monomers containing an alkylaminoalkyl group, such as aminoethyl (meth)acrylate, dimethylaminoethyl (meth)acrylate and tert-butylaminoethyl (meth)acrylate; alkoxyalkyl (meth)acrylates such as methoxyethyl (meth)acrylate and ethoxyethyl (meth)acrylate; (meth)acrylates containing an alkoxy group (or an ether bond in a side chain), such as tetrahydrofurfuryl (meth)acrylate, methoxyethylene glycol (meth)acrylate, methoxydiethylene glycol (meth)acrylate, methoxypolyethylene glycol (meth)acrylate and methoxypolypropylene glycol (meth)acrylate; and vinyl monomers such as (meth)acrylonitrile, vinyl acetate, vinyl propionate, N-vinylpyrrolidone, methyl vinyl pyrrolidone, vinyl pyridine, vinyl piperidine, vinyl pyrimidine, vinyl piperazine, vinyl pyrazine, vinyl pyrol, vinyl imidazole, vinyl caprolactam, vinyl oxazole and vinyl morpholine. Of the above, (meth)acrylic acid, hydroxyethyl (meth)acrylate, 2-methoxyethyl acrylate, acrylamide, N-vinyl-2-pyrrolidone and diacetone acrylamide are preferably used. Either one of these substances or a mixture thereof can be used in the copolymerization. These copolymerizable monomers are used to control the cohesive power of the gel layer and improve the solubility of the drug. The amounts of these monomers can be arbitrarily selected depending on the purpose.

Of the above-described acrylate polymers, a copolymer obtained by copolymerizing the alkyl (meth)acrylate with monomer(s) represented by formulae (I) and/or (II):

$$CH_2=CHX \qquad (I)$$

$$CH_2=CRY \qquad (II)$$

wherein R represents a hydrogen atom or a methyl group; X represents a group having at least one nitrogen atom or a nitrogen atom and an oxygen atom; Y represents a hydrogen atom or —COOR'; and R' represents a group having at least one nitrogen atom or a nitrogen atom and an oxygen atom, or a hydroxyl lower alkyl group, is preferably used in the present invention. By copolymerizing the monomers represented by formulae (I) and (II), the extent of crosslinking and the properties of the gel obtained can be controlled. The weight ratio of the (meth)acrylate to the monomer(s) of formulae (I) and/or (II) is preferably (40-99)/(1-60), more preferably (60-98)/(2-40) while the total amount of these monomers being 100.

It is also preferred in the present invention to use as the acrylate copolymer a copolymer obtained by copolymerizing the alkyl (meth)acrylate and monomer(s) containing a carboxyl group and/or a hydroxyl group. The weight ratio of the alkyl (meth)acrylate to the monomer(s) containing a carboxyl group and/or a hydroxyl group is (90-99)/(1-10). The monomer(s) containing a carboxyl group and/or a hydroxyl group is a component which improves a cohesive power and an adhesiveness of the gel layer.

It is more preferred in the present invention to use as the acrylate polymer a copolymer obtained by copolymerizing the alkyl (meth)acrylate, the monomer(s) of the formulae (I) and/or (II) as defined above, and monomer(s) containing a carboxyl group and/or a hydroxyl group. The amount of the monomer(s) containing a carboxyl group and/or a hydroxyl group is preferably 1 to 10% by weight based on the weight of the copolymer obtained. In this case, the weight ratio of the alkyl (meth)acrylate, the monomer(s) of formulae (I) and/or (II), and the monomer(s) containing a carboxyl group and/or a hydroxyl group is (50-99)/(0-40)/(1-10).

The liquid ingredient used in the present invention has a high compatibility with the acrylate copolymer. The liquid ingredient appropriately plasticizes the crosslinked gel layer and thus imparts a flexible texture to the layer to thereby relive a pain or skin irritativeness caused by the skin adhesiveness upon the separation of the crosslinked gel layer from the skin surface.

Therefore, the liquid ingredient can be selected from materials having a plasticizing effect. A substance which further has an absorption-promoting effect can preferably be selected to improve the percutaneous absorption of the drug component used together.

Examples of the liquid ingredient include glycols such as ethylene glycol, diethylene glycol, triethylene glycol, propylene glycol, polyethylene glycol and polypropylene glycol; fats and oils such as olive oil, castor oil, squalene and lanolin; organic solvents such as dimethyl decyl sulfoxide, methyl octyl sulfoxide, dimethyl sulfoxide, dimethylformamide, dimethylacetamide, dimethyllaurylamide, dodecyl pyrrolidone and isosorbitol; liquid surfactants; plasticizers such as diisopropyl adipate, phthalates and diethyl sebacate; hydrocarbons such as liquid paraffin; ethoxylated stearyl alcohol, glycerol esters, isopropyl myristate, isotridecyl myristate, ethyl laurate, N-methylpyrrolidone, ethyl oleate, oleic acid, isopropyl adipate, isopropyl palmitate, octyl palmitate and 1,3-butanediol. Of the above, phthalates, isopropyl myristate, isotridecyl myristate and octyl palmitate are preferably used. These substances can be used alone or as a mixture thereof.

The acrylate polymer and the liquid ingredient are contained in the crosslinked gel layer at a weight ratio of preferably from 1.0/0.25 to 1.0/2.0, more preferably from 1.0/0.4 to 1.0/2.0 and most preferably from 1.0/0.6 to 1.0/1.8, from the standpoint of reducing the skin irritativeness. Namely, it is preferred to use a considerably large amount of the liquid ingredient. In contrast, a conventional preparation usually contains a liquid ingredient at a weight ratio less than 1.0/0.25. Such a low content of the liquid ingredient would sometimes make it impossible to achieve a satisfactory low level of the skin irritativeness, from a practical standpoint.

In the present invention, the composition thus-obtained is then crosslinked by an appropriate crosslinking procedure to prepare a gel, thus preventing the leakage of the liquid ingredient contained in the preparation and imparting a cohesive power, as described above. The crosslinking can be effected by a physical means such as irradiation (for example, UV irradiation or electron beam irradiation) or a chemical means using a crosslinking agent (for example, polyisocyanate compound, organic peroxide, organic metal salt, metal alcoholate, metal chelate compound, polyfunctional compound).

Of these crosslinking procedures, irradiation or use of an organic peroxide might induce decomposition in the cases of some drug component. Further, the use of a highly reactive isocyanate or a metal salt or an organic metal salt commonly used in crosslinking reaction might sometimes cause an increase in the viscosity of the solution, which lowers the workability thereof. It is also possible to preliminarily copolymerize a polyfunctional monomer such as diacrylate with the acrylate polymer. In this case, however, there is a possibility that the viscosity of the solution would increase at the polymerization.

In the present invention, therefore, it is preferred to select trifunctional isocyanate or a metal alcoholate or a metal chelate compound comprising titanium or aluminum from the above-described crosslinking agents, from the standpoints of reactivity and handling. These crosslinking agents would not cause any increase in the viscosity of the solution until the completion of the application and drying, which means that they are excellent in workability. When these crosslinking agents are used, the crosslinking reaction can be effected to a certain extent by coating and drying the gel layer, but the coated and dried gel layer is preferably aged at from 40° to 70° C. to stabilize the properties of the gel layer. The aging time varies depending on the addition amount and the kind of the functional groups of the crosslinking agent, and is generally from 2 to 3 days. Such a crosslinking agent is preferably used in an amount of from 0.01 to 2.0 parts by weight per 100 parts by weight of the acrylate polymer. When the acrylate polymer does not have a functional group which reacts with the above-described crosslinking agent, the material to be crosslinked may be modified by, for example, treating with an alkali to thereby enable the crosslinking.

In the present invention, a drug component can be added to the crosslinked gel layer thus-obtained to thereby prepare an oily gel preparation. The drug component added can be arbitrarily selected depending on the purpose of the treatment. Namely, any drug component can be used so long as it can be percutaneously absorbed. Examples thereof include cortisteroid, analgesic/antiinflammatory agent, hypnotic/sedative agent, ataraxic, antihypertensive agent, hypotensive diuretic, antibiotic, anesthetic, antibacterial agent, fungicide, vitamin preparation, coronary dilator (except isosorbide dinitrate), antihistamine, antitussive agent, sex hormone (except estrogen), antidepressant, cerebral circulatory improver, antivommiting agent, antitumor agent and biogenic. These drugs can be used alone or as a mixture thereof. To achieve the uniform dispersion in the crosslinked gel layer and promote percutaneous absorption, it is preferred to select and use a hydrophobic drug (having a solubility of 0.4 g/100 ml of water or less at room temperature) from the above-described drug components.

The content of the drug component can be appropriately determined depending on the drug component selected and the purpose of the administration. It is generally contained in the crosslinked gel layer in an amount of from 1 to 40% by weight, preferably from 3 to 30% by weight, based on the weight of the crosslinked gel layer. If the content of the drug is smaller than 1% by weight, the release of a therapeutically effective amount of the drug cannot be expected. If it is exceeds 40% by weight, on the other hand, no improvement in the effect cannot be achieved any more. Thus, both of these cases bring about economical disadvantages.

The method for preparing the oily gel material and the oily gel preparation according to the present invention is not particularly limited. For example, a drug solution is added to a solution of an acrylate polymer followed by stirring, and a liquid ingredient is added thereto to from a uniform solution. A crosslinking agent in the form of a solution is added to the above-obtained solution and the viscosity of the resulting solution is adjusted by ethyl acetate to prepare a gel layer coating composition. The coating composition is coated on a separator, and then dried to form an oily gel layer. The thickness of the oily gel layer after drying is preferably from 10 to 300 μm, and more preferably from 40 to 150 μm. The resulting oily gel layer is transferred to a substrate, and then, if necessary, aged at from 40° to 70° C. to obtain an oily gel preparation according to the present invention. An oily gel bioadhesive material according to the present invention can be prepared in the same manner as above except that the drug solution is not used.

When the drug component is added to the acrylic oily gel preparation of the present invention, it is preferred that the crosslinked gel layer contains the drug as described above. Alternatively, it is possible that the drug component is not contained in the crosslinked gel layer but is dissolved in an appropriate solvent, and the solution thus-obtained is located at the interface between the crosslinked gel layer and the substrate, followed by sealing the periphery of the preparation. When the layer containing the drug component is separated from the cross-linked gel layer in the manner as described above, the decomposition of the drug component upon storage can be suppressed in the case of a drug component which is liable to undergo decomposition. In this case, the release of the drug component can be severely controlled by locating a microporous film between the layer containing the drug component and the crosslinked gel layer.

Each of the acrylic oily gel bioadhesive material and the acrylic oily gel preparation of the present invention, which has the above-described structure, comprises a crosslinked gel layer containing a large amount of the liquid ingredient compatible with the acrylate polymer. Thus, it is possible to impart a flexibility to the crosslinked gel layer and to reduce the skin irritativeness while maintaining the cohesive power of the gel layer. When the preparation of the present invention is separated from the surface of the skin, therefore, the pain and skin irritativeness caused by the adhesiveness can be reduced. Thus, the percutaneous gel preparation of the present invention has well-balanced adhesiveness to the skin and nonirritativeness. Further, the acrylic oily gel preparation containing a drug component can appropriately release the drug component onto the surface of the skin. Thus, it is useful to prevent and treat various diseases through the percutaneous administration of the drug component.

In the present invention, the standard of the painless removal of the oily gel preparation from the surface of the skin is specified as follows. In a peeling test by volunteers, the amount of the peeled horny substance caused by the removal of the preparation of the present invention corresponds to 1/5 to ⅔ of those observed in the case of control preparations free from any liquid ingredient. When the amount of the peeled horny substance is outside the above range, either a pain or an insufficient skin-adhesion might be caused.

The present invention will be described in more detail by reference to the following Examples and Comparative Examples, but the present invention is not construed as being limited thereto. In the following Examples and Comparative Examples, all parts and percents are by weight.

EXAMPLE 1

95 Parts of 2-ethylhexyl acrylate and 5 parts of acrylic acid were copolymerized in ethyl acetate under an inert gas atmosphere to prepare an acrylate polymer solution.

To 50 parts of the solid content of the above solution, 50 parts of isopropyl myristate was added. To 99.8 parts of the above acrylic polymer, 0.2 parts of aluminum tris(acetylacetonate) which was in the form of a 10% solution in acetylacetone was added. Further, ethyl acetate was added thereto to adjust the viscosity of the mixture.

The viscous solution thus-obtained was applied to a polyester separator (thickness: 75 μm) at a dry thickness of 80 μm. After drying and crosslinking, a crosslinked gel layer was formed.

The crosslinked gel layer thus-obtained was adhered to the nonwoven fabric face of a laminate film (i.e., a substrate), which was obtained by extruding polyester having a thickness of 2 μm on a polyester nonwoven fabric (12 g/m$^2$). Thus, an acrylic oily gel bioadhesive material of the present invention was obtained.

EXAMPLE 2

The procedure of Example 1 was repeated except that 45 parts of isopropyl myristate and 10 parts of ketoprofen were added to 45 parts of the solid content of the acrylate polymer obtained in Example 1. Thus, an acrylic oily gel preparation of the present invention was obtained.

EXAMPLE 3

The procedure of Example 2 was repeated except that the isopropyl myristate was replaced by octyl palmitate. Thus, an acrylic oily gel preparation of the present invention was obtained.

COMPARATIVE EXAMPLE 1

The procedure of Example 1 was repeated except that the acrylate polymer prepared in Example 1 was not subjected to the crosslinking but was directly used. Thus, an acrylic gel material containing the liquid ingredient was obtained.

This acrylic gel material was broken because of low cohesion power. Thus, it was impossible to subject the material to any of the tests which will be described hereinafter

COMPARATIVE EXAMPLE 2

The procedure of Example 1 was repeated except that 10 parts of ketoprofen was added to 90 parts of the solid content of the acrylate polymer solution prepared in Example 1, followed by adding ethyl acetate, to adjust the viscosity. Thus, an uncrosslinked acrylic preparation free from any liquid ingredient was obtained.

COMPARATIVE EXAMPLE 3

The procedure of Comparative Example 2 was repeated except that 0.2 part of a crosslinking agent (aluminum tris(acetylacetonate)) was added to the polymer solid content. Thus, a crosslinked acrylate preparation free from any liquid ingredient was obtained.

EXAMPLE 4

75 Parts of 2-ethylhexyl acrylate, 23 parts of N-vinyl-2-pyrrolidone and 2 parts of acrylic acid were copolymerized in ethyl acetate under an inert gas atmosphere to prepare an acrylate polymer solution.

To 50 parts of the solid content of the above solution, 50 parts of octyl palmitate was added. To 99.8 parts of the above acrylic polymer, 0.2 parts of ethylacetoacetate aluminum diisopropylate which was in the form of a 10% solution in acetylacetone was added. Further, ethyl acetate was added thereto to adjust the viscosity of the mixture.

The viscous solution obtained above was treated in the same manner as in Example 1 to prepare an acrylic oily gel bioadhesive material of the present invention.

EXAMPLE 5

The procedure of Example 4 was repeated except that 40 parts of octyl palmitate and 15 parts of nifedipine were added to 45 parts of the solid content of the acrylate polymer prepared in Example 4. Thus, a crosslinked gel layer was formed.

The same procedure as in Example 1 was followed except that the polyester film used as a substrate in Example 1 on which aluminum was vapor-deposited for light shielding was used. Thus, an acrylic oily gel preparation of the present invention was obtained.

EXAMPLE 6

The procedure of Example 5 was repeated except that octyl palmitate was replaced with isotridecyl myristate. Thus, an acrylic oily gel preparation of the present invention was obtained.

COMPARATIVE EXAMPLE 4

The procedure of Example 4 was repeated except that the acrylate polymer prepared in Example 4 was not subjected to the crosslinking but was directly used. Thus, an uncrosslinked acrylic gel plaster free from any liquid ingredient was obtained.

This acrylic gel plaster was broken because of low cohesive power. Thus, it was impossible to subject the plaster to any of the tests which will be described hereinafter.

COMPARATIVE EXAMPLE 5

The procedure of Example 4 was repeated except that 15 parts of nifedipine was added to 85 parts of the solid content of the acrylate polymer solution prepared in Example 4, followed by adding ethyl acetate, to adjust the viscosity. Thus, an uncrosslinked acrylic preparation free from any liquid ingredient was obtained.

COMPARATIVE EXAMPLE 6

The procedure of Comparative Example 5 was repeated except that 0.2 part of a crosslinking agent (ethylacetoacetate aluminum diisopropylate) was added to the polymer solid content. Thus, a crosslinked acrylate preparation free from any liquid ingredient was obtained.

COMPARATIVE EXAMPLE 7

The procedure of Comparative Example 4 was repeated except that the acrylate polymer used in Comparative Example 4 was replaced with a polyisobutyrene rubber polymer comprising 10 parts of polyisobutyrene (viscosity-average molecular weight: 990,000), 15 parts of polyisobutyrene (viscosity-average molecular weight: 60,000), 3 parts of polyisobutyrene (viscosity-average molecular weight: 1260) and 7 parts of an alicyclic petroleum resin (softening point: 100° C.), and ethyl acetate was replaced with toluene. Thus, a rubber gel preparation was obtained.

This gel preparation showed precipitation of a large amount of nifedipine immediately after the completion of the preparation.

EXAMPLE 7

70 Parts of 2-ethylhexyl acrylate, 25 parts vinyl acetate and 5 parts of 2-hydroxyethyl methacrylate were copolymerized in ethyl acetate under an inert gas atmosphere to prepare an acrylate polymer solution.

To 50 parts of the solid content of the above solution, 50 parts of isotridecyl myristate was added. To 99.7 parts of the above acrylic polymer, 0.3 parts of trifunctional isocyanate ("Coronate HL" manufactured by Nippon Polyurethane Co., Ltd.) in the form of a 10% solution in ethyl acetate was added. Further, ethyl acetate was added thereto to adjust the viscosity.

The viscous solution thus-obtained was treated in the same manner as in Example 1 to prepare an acrylic oily gel bioadhesive material of the present invention.

EXAMPLE 8

The procedure of Example 7 was repeated except that 45 parts of tridecyl myristate and 10 parts of clonidine were added to 45 parts of the solid content of the acrylate polymer prepared in Example 7 and 0.3 part of trifunctional isocyanate ("Coronate HL" manufactured by Nippon Polyurethane Co., Ltd.) in the form of a 10% solution in ethyl acetate was added to 99.7 parts of the acrylate polymer. Thus, a crosslinked gel layer was formed. The crosslinked gel layer was adhered to the same type of the substrate as used in Example 1 to prepare an acrylic gel oily preparation of the present invention.

EXAMPLE 9

The procedure of Example 8 was repeated except that isotridecyl myristate was replaced with isopropyl myristate. Thus, an acrylic oily gel preparation of the present invention was obtained.

COMPARATIVE EXAMPLE 8

The procedure of Example 7 was repeated except that the crosslinking agent was not added. Thus, an uncrosslinked acrylic gel material containing a liquid ingredient was obtained.

This acrylic gel material was broken because of low cohesive power. Thus, it was impossible to subject the material to any of the tests which will be described hereinafter.

COMPARATIVE EXAMPLE 9

The procedure of Example 7 was repeated except that 0.3 part of trifunctional isocyanate ("Coronate HL" manufactured by Nippon Polyurethane Co., Ltd.) in the form of a 10% solution in ethyl acetate was added to 99.7 parts of the solid content of the acrylate polymer solution prepared in Example 7, followed by adjusting the viscosity with ethyl acetate. Thus, a crosslinked acrylic plaster free from any liquid ingredient was obtained.

COMPARATIVE EXAMPLE 10

The procedure of Example 7 was repeated except that 10 parts of clonidine was added to 90 parts of the solid content of the acrylate polymer solution prepared in Example 7 and 0.3 part of trifunctional isocyanate ("Coronate HL" manufactured by Nippon Polyurethane Co., Ltd.) in the form of a 10% solution in ethyl acetate was added to 99.7 parts of the solid content of the acrylate polymer solution prepared in Example 7, followed by adjusting the viscosity with ethyl acetate. Thus, a crosslinked acrylic preparation free from any liquid ingredient was obtained.

COMPARATIVE EXAMPLE 11

By using the acrylate polymer solution prepared in Example 1, a plaster which did contain the liquid ingredient, crosslinking agent and drug component was prepared. The substrate used was the same type as used in Example 1.

COMPARATIVE EXAMPLE 12

The procedure of Example 1 was repeated except that 18 parts of isopropyl myristate was added to 82 parts of the solid content of the acrylate polymer solution. Thus, an acrylic gel material was obtained.

COMPARATIVE EXAMPLE 13

20 Parts of CARBOPOL ® 940 (molecular weight: 4,000,000), 40 parts of isopropyl myristate and 10 parts of an ethoxidized nonionic surfactant (TERGITOL 15-15-12, manufactured by Union Carbide Co.) were dissolved in 10 parts of water, and the resulting mixture was stirred. However, since isopropyl myristate did not dissolve in water, CARBOPOL and the isopropyl myristate were not mixed and it was impossible to prepare a gel material.

COMPARATIVE EXAMPLE 14

5 Parts of CARBOPOL 940 was dissolved in 35 parts of water with stirring. The resulting solution was allowed to stand at room temperature for 24 hours.

Separately, a solution was prepared by dissolving 30 parts of isopropyl myristate and 10 parts of TERGITOL 15-15-12 into 20 parts of water. This solution was mixed with the solution obtained above, and the mixed solution was stirred with a high speed disper.

After degassing, the solution was flow-cast on a metallic mold having a depth of 3 mm, and heated at 50° C. for 1 hour to gel the solution. The gel layer is laminated on the same type of the substrate as used in Example 1 to prepare a gel material.

This gel material showed severe oozing of isopropyl myristate and did not substantially have adhesiveness to the skin. Therefore, it was impossible to subject the gel material to any of the tests.

COMPARATIVE EXAMPLE 15

A 30% polyhydroxyethyl methacrylate in dimethyl formamide was flow-cast on a Teflon plate, and dried to obtain a film having a thickness of about 100 μm.

0.3 g of 30–40 mesh sieve pass CARBOPOL 940 was introduced in 60 ml of a water/dimethyl formamide (3/1) mixed solution. 10 ml of this solution was uniformly sprayed on a piece of 50 cm$^2$ (7.1 cm×7.1 cm) obtained by cutting the film obtained above and wetting with dimethyl formamide, and dried at room temperature to prepare a gel material.

This material did not have adhesiveness to the skin, and it was impossible to subject the material to any of the tests.

COMPARATIVE EXAMPLE 16

The gel material obtained in Comparative Example 15 above was dipped in water for 1 hour to wet the same. The wet gel material had a relatively good adhesiveness to the skin. However, the gel material had a very weak adhesive strength and easily separated from the skin. Further, the adhesive layer portion thereof was broken by a slight force because of low cohesion power. Therefore, it was impossible to subject the wet gel material to any of the tests.

Further, the wet gel material had the tendency to dry easily, and moisture in the gel material volatilized during bonding to the skin, thereby losing the adhesive strength.

TEST EXAMPLE

Each of the gel materials and gel preparations obtained in the above Examples and Comparative Examples was stored at 40° C. under a relative humidity of 75% for 2 weeks. These samples were then subjected to the following tests. In the determination of the peeled horny substance, samples comprising a single-layer film (thickness: 9 μm) having no nonwoven fabric laminated as the substrate were employed, since the absorption of the dyeing solution by the nonwoven fabric in the substrate might substantially lower the accuracy of the determination. Further, the preparations containing clonidine were not subjected to the human patch test. Tables 1 and 2 show the results.

Rabbit Patch Test

Each of the samples obtained in the Examples and the Comparative Examples was applied onto the dorsal part of a rabbit from which the hair had been removed. Then, 2 mol portions of the blood of the rabbit were collected after 1.0, 2.5, 4.0, 6.0 and 8.0 hours, and the concentration of isosorbide dinitrate in each blood sample was determined by gas chromatography. The samples containing clonidine were cut into a piece of 3 cm$^2$ (1.73 cm×1.73 cm) while the others were cut into a piece of 50 cm$^2$ (7.1 cm×7.1 cm).

ADHESION TEST

Each sample in the form of a strip of 12 mm in width was applied to a bakelite plate. Then, a roller of a load of 300 g was moved thereon back and force to secure the adhesion of the sample to the plate. Subsequently, the sample was peeled off in the direction of 180° C. at a rate of 300 mm/min, and the peeling force upon this procedure was measured.

Tack Test

The tack of each sample was evaluated by the probe tack method with a rheometer.

The sample was fixed on a metal plate in a manner such that the face to be adhered to the skin was placed upward. Then, a spherical probe (diameter: 10 mm) was contacted with the sample under a load of 100 g at a rate of 2 cm/min. After maintaining this state for 20 seconds, the spherical probe was separated therefrom at the same rate. The peeling force upon this procedure was measured.

Pain At Peeling

Samples were applied to the inside of upper arms of 5 volunteers. After 30 minutes, the samples were peeled off and the pain thus caused was examined. The pain was evaluated in five grades (1: the least pain) and expressed in the average of the volunteers. As a standard, the sample prepared in Comparative Example 1 was referred to as 5.

Peeled Horny Substance

Circular samples (diameter: 16 mm) were applied to the inside of upper arms of 3 volunteers (A, B and C). After 30 minutes, the samples were peeled off and immersed in a dyeing solution composed of 0.5% of Gentian violet, 0.5% of Brillian green and 98.5% of distilled water for 3 minutes, followed by washing with water, to dye horny cells.

These samples were then immersed in a 5% aqueous solution of sodium dodecyl sulfate over day and night to extract the dyeing solution. The absorbance of the extract was measured at 595 nm to compare the number of the peeled horny cells. That is, it was considered that a higher absorbance would indicate the larger amount of the peeled horny substance.

A good correlation was observed between the number of the peeled horny cells counted with a stereoscopic microscope and the above-described absorbance.

TABLE 1

| | Rabbit patch test | |
|---|---|---|
| | Maximum blood level (ng/ml) | Time required for achieving maximum blood level (hour) |
| Example 2 | 2,970 | 2.0 |
| Example 3 | 2,840 | 2.0 |
| Example 5 | 205 | 4.0 |
| Example 6 | 198 | 4.0 |
| Example 8 | 16 | 6.0 |
| Example 9 | 20 | 6.0 |
| Comparative Example 2 | 1,840 | 2.0 |
| Comparative Example 3 | 1,510 | 2.0 |
| Comparative Example 5 | 58 | 4.0 |
| Comparative Example 6 | 49 | 4.0 |
| Comparative Example 7 | 11 | 4.0 |
| Comparative Example 10 | 8 | 6.0 |

TABLE 2

| | Adhesiveness (g) | Tack (g) | Pain | Peeled horny substance(*) | | |
|---|---|---|---|---|---|---|
| | | | | A | B | C |
| Example 1 | 184 | 45 | 1.6 | 43.4 | 44.4 | 27.4 |
| Example 2 | 176 | 43 | 1.6 | 48.7 | 40.1 | 33.8 |
| Example 3 | 181 | 44 | 1.8 | 42.2 | 39.5 | 34.1 |
| Example 4 | 156 | 38 | 1.4 | 35.1 | 38.6 | 29.9 |
| Example 5 | 142 | 34 | 1.4 | 37.2 | 36.6 | 35.5 |
| Example 6 | 180 | 44 | 1.6 | 49.1 | 45.5 | 28.7 |
| Example 7 | 151 | 36 | 1.2 | 36.1 | 37.2 | 31.3 |
| Example 8 | 154 | 37 | — | — | — | — |
| Example 9 | 132 | 32 | — | — | — | — |
| Comparative Example 2 | 532 | 129 | 5.0 | 148 | 162 | 131 |
| Comparative Example 3 | 516 | 125 | 5.0 | 162 | 181 | 141 |
| Comparative Example 5 | 451 | 109 | 4.6 | 159 | 132 | 124 |
| Comparative Example 6 | 484 | 117 | 4.8 | 179 | 132 | 138 |
| Comparative Example 7 | 1,187 | 282 | 5.0 | 140 | 70.1 | 72.2 |
| Comparative Example 9 | 421 | 102 | 4.6 | 141 | 125 | 119 |
| Comparative Example 10 | 432 | 105 | — | — | — | — |
| Comparative Example 11 | 529 | 138 | 5.0 | 151 | 192 | 138 |
| Comparative Example 12 | 531 | 140 | 4.6 | 141 | 106 | 122 |

As is apparent from Tables 1 and 2 above, the acrylic oily gel bioadhesive material and the acrylic oily gel preparation of the present invention show less pain at the peeling and also suffer from the peeling of a smaller amount of the horny substance, as compared with the products of Comparative Examples. Further, it is apparent that in the gel preparation containing the drug component, a large amount of the drug can be rapidly absorbed percutaneously.

While the invention has been described in detail and with reference to specific examples thereof, it will be apparent to one skilled in the art that various changes and modifications can be made therein without departing from the spirit and scope thereof.

What is claimed is:

1. An acrylic oily gel bioadhesive material comprising a substrate having on one surface thereof a crosslinked gel layer which is a non-aqueous system formed by crosslinking a composition comprising an acrylate polymer comprising as a main component an alkyl (meth)acrylate having four or more carbon atoms in the alkyl moiety and a liquid ingredient compatible with said acrylate polymer, wherein the weight ratio of said acrylate polymer to said liquid ingredient is from 1.0/0.25 to 1.0/2.0; said crosslinking is effected by using a crosslinking agent selected from the group consisting of a metal alcoholate and a metal chelate each comprising titanium or aluminum, and trifunctional isocyanate; and said acrylate polymer is selected from the group consisting of:

(a) a copolymer obtained by copolymerizing the alkyl (meth)acrylate with at least one monomer represented by at least one of formulae (I) and (II):

$$CH_2=CHX \qquad (I)$$

$$CH_2=CRY \qquad (II)$$

wherein R represents a hydrogen atom or a methyl group; X represents a group having at least one nitrogen atom or a nitrogen atom and an oxygen atom; Y represents a hydrogen atom or —COOR′; and R′ represents a group having at least one nitrogen atom or a nitrogen atom and an oxygen atom, or a hydroxy lower alkyl group, and wherein the weight ratio of the alkyl (meth)acrylate to the at least one monomer represented by at least one of formulae (I) and (II) is (40–99)/(1–60);

(b) a copolymer obtained by copolymerizing the alkyl (meth)acrylate with ate least one monomer containing at least one of a carboxyl group and a hydroxyl group, and wherein the weight ratio of the alkyl (meth)acrylate to the at least one monomer containing at least one of a carboxyl group and a hydroxyl group is (90–99)/(1–10); and (c) a copolymer obtained by copolymerizing the alkyl (meth)acrylate with at least one monomer represented by at least one of formulae (I) and (II):

$$CH_2=CHX \qquad (I)$$

$$CH_2=CRY \qquad (II)$$

wherein R represents a hydrogen atom or a methyl group; X represents a group having at least one nitrogen atom or a nitrogen atom and an oxygen atom; Y represents a hydrogen atom or —COOR′; and R′ represents a group having at least one nitrogen atom or a nitrogen atom and an oxygen atom, or a hydroxy lower alkyl group, and at least one monomer containing at least one of a carboxyl group and a hydroxyl group, wherein the amount of said at least one monomer containing at least one of a carboxyl group and a hydroxyl group is 1 to 10% by weight based on the weight of the copolymer, and wherein the weight ratio of the alkyl (meth)acrylate, the at least one monomer represented by formulae (I) and (II), and the at least one monomer containing at least one of a carboxyl group and a hydroxyl group is (50–90)/(0–40)/(1–10).

2. An acrylic oily gel bioadhesive material as claimed in claim 1, wherein the weight ratio of said acrylate polymer to said liquid ingredient is from 1.0/0.4 to 1.0/2.0.

3. An acrylic oily gel bioadhesive material as claimed in claim 2, wherein the weight ratio of said acrylate polymer to said liquid ingredient is from 1.0/0.6 to 1.0//1.8.

4. An acrylic gel bioadhesive material as claimed in claim 1, wherein said liquid ingredient compatible with said acrylate polymer is selected from the group consisting of glycols, fats and oils, organic solvents, liquid surfactants, hydrocarbons, ethoxylated stearyl alcohol, glycerol esters, isopropyl myristate, isotridecyl myristate, ethyl laurate, N-methyl-pyrrolidone, ethyl oleate, oleic acid, isopropyl adipate, isopropyl palmitate, octyl palmitate and 1,3-butanediol.

5. An acrylic oily gel preparation wherein a drug component is contained in an acrylic oily gel bioadhesive material as claimed in claim 1.

6. An acrylic oily gel preparation as claimed in claim 5, wherein the content of said drug component is from 1 to 40% by weight based on the total amount of said crosslinked gel layer.

7. An acrylic oily gel preparation as claimed in claim 6, wherein the content of said drug component is from 3 to 30% by weight based on the total amount of said crosslinked gel layer.

8. An acrylic oily gel preparation as claimed in claim 5, wherein the thickness of said crosslinked gel layer is from 10 to 300 $\mu$m.

9. An acrylic oily gel preparation as claimed in claim 8, wherein the thickness of said crosslinked gel layer is from 40 to 150 $\mu$m.

* * * * *